US006673114B2

(12) United States Patent
Hartdegen et al.

(10) Patent No.: US 6,673,114 B2
(45) Date of Patent: Jan. 6, 2004

(54) MULTI MODULAR TRIALING SYSTEM AND INSTRUMENTATION

(75) Inventors: Vernon R. Hartdegen, Collierville, TN (US); Dean Hughes, Cordova, TN (US)

(73) Assignee: Smith & Nephew, Inc., Memphis, TN (US)

( * ) Notice: Subject to any disclaimer, the term of this patent is extended or adjusted under 35 U.S.C. 154(b) by 264 days.

(21) Appl. No.: 09/845,459

(22) Filed: Apr. 30, 2001

(65) Prior Publication Data

US 2001/0053935 A1 Dec. 20, 2001

Related U.S. Application Data

(60) Provisional application No. 60/201,503, filed on May 3, 2000.

(51) Int. Cl.[7] .................................................. A61F 2/40
(52) U.S. Cl. .................. 623/19.12; 623/18.11; 623/19.11
(58) Field of Search ............... 623/18.11, 19.11–19.14, 623/22.11–22.14, 23.11–23.27; 606/85

(56) References Cited

U.S. PATENT DOCUMENTS

| | | |
|---|---|---|
| 3,694,820 A | 10/1972 | Scales et al. |
| 3,803,641 A | 4/1974 | Golyakhovsky |
| 4,001,896 A | 1/1977 | Arkangel |
| 4,045,825 A | 9/1977 | Stroot |
| 4,106,130 A | 8/1978 | Scales |
| 4,135,517 A | 1/1979 | Reale |
| 4,179,758 A | 12/1979 | Gristina |
| 4,224,695 A | 9/1980 | Grundei et al. |
| 4,268,920 A | 5/1981 | Engelbrecht et al. |
| 4,538,305 A | 9/1985 | Engelbrecht et al. |
| 4,676,797 A | 6/1987 | Anapliotis et al. |
| 4,676,798 A | 6/1987 | Noiles |
| 4,714,476 A | 12/1987 | Ranawat et al. |

(List continued on next page.)

FOREIGN PATENT DOCUMENTS

| | | |
|---|---|---|
| DE | 163 476 | 6/1958 |
| DE | 29 27 880 | 2/1981 |
| DE | 43 20 086 A1 | 12/1994 |
| EP | 0 099 167 A1 | 1/1984 |
| EP | 0 177 755 A1 | 9/1985 |
| EP | 0 363 019 A2 | 4/1990 |
| EP | 0 457 222 A1 | 5/1991 |
| EP | 0 679 375 A1 | 11/1995 |
| EP | 0 853 930 A2 | 7/1998 |
| EP | 0 679 375 | 9/1998 |
| EP | 0 931 522 A1 | 7/1999 |
| EP | 0 712 617 | 9/1999 |
| EP | 0 940 126 A1 | 9/1999 |
| EP | 0 993 813 A2 | 4/2000 |
| EP | 1 048 274 A2 | 11/2000 |
| EP | 1 082 943 A2 | 3/2001 |
| FR | 2 288 509 | 5/1976 |
| FR | A 2 664 809 | 1/1992 |
| FR | 2 669 214 | 5/1992 |
| FR | 2 685 633 | 7/1993 |
| FR | 2 697 996 | 5/1994 |
| FR | 2 721 200 | 12/1995 |
| FR | 2 763 501 | 11/1998 |
| FR | 2 773 469 | 7/1999 |
| GB | 1 575 278 | 9/1980 |
| GB | 2 253 147 A | 9/1992 |
| GB | 2 334 890 A | 3/1999 |
| WO | WO 96/17553 * | 6/1996 .............. 623/19.12 |
| WO | WO 98/46172 | 10/1998 |
| WO | WO 00/06056 | 2/2000 |

OTHER PUBLICATIONS

Bechtold,, Joan, Cross–Sectional Geometry of Tibiae, (1989).

(List continued on next page.)

*Primary Examiner*—Pedro Philogene
(74) *Attorney, Agent, or Firm*—Kilpatrick Stockton LLP

(57) ABSTRACT

Methods, instrumentation and devices for humeral implant positioning, including an improved trialing system utilizing an adjustment instrument and orientation indicia.

215 Claims, 6 Drawing Sheets

U.S. PATENT DOCUMENTS

| | | | |
|---|---|---|---|
| 4,731,086 A | 3/1988 | Whiteside et al. | |
| 4,790,854 A | 12/1988 | Harder et al. | |
| 4,822,365 A | 4/1989 | Walker et al. | |
| 4,822,366 A | 4/1989 | Bolesky | |
| 4,834,081 A | 5/1989 | Van Zile | |
| 4,865,605 A | 9/1989 | Dines et al. | |
| 4,883,488 A | 11/1989 | Bloebaum et al. | |
| 4,919,670 A | 4/1990 | Dines et al. | |
| 4,936,853 A | 6/1990 | Fabian et al. | |
| 4,944,764 A | 7/1990 | Stossei | |
| 4,950,297 A | 8/1990 | Elloy et al. | |
| 4,950,298 A | 8/1990 | Gustilo et al. | |
| 4,959,071 A | 9/1990 | Brown et al. | |
| 4,963,155 A | 10/1990 | Lazzeri et al. | |
| 4,985,037 A | 1/1991 | Petersen | |
| 5,002,578 A | 3/1991 | Luman | |
| 5,071,438 A | 12/1991 | Jones et al. | |
| 5,100,407 A | 3/1992 | Conrad et al. | |
| 5,123,928 A | 6/1992 | Moser | |
| 5,133,760 A | 7/1992 | Petersen et al. | |
| 5,133,763 A | 7/1992 | Mullers | |
| 5,135,529 A * | 8/1992 | Paxson et al. | 606/85 |
| 5,139,521 A | 8/1992 | Schelhas | |
| 5,152,796 A | 10/1992 | Slamin | |
| 5,194,066 A | 3/1993 | Van Zile | |
| 5,207,711 A | 5/1993 | Caspari et al. | |
| 5,226,915 A | 7/1993 | Bertin | |
| 5,271,737 A | 12/1993 | Baldwin et al. | |
| 5,290,313 A | 3/1994 | Heldreth | |
| 5,314,479 A | 5/1994 | Rockwood, Jr. et al. | |
| 5,330,534 A | 7/1994 | Herrington et al. | |
| 5,358,526 A * | 10/1994 | Tornier | 623/19.14 |
| 5,387,240 A | 2/1995 | Pottenger et al. | |
| 5,462,563 A | 10/1995 | Shearer et al. | |
| 5,489,309 A | 2/1996 | Lackey et al. | |
| 5,507,814 A | 4/1996 | Gilbert et al. | |
| 5,507,817 A * | 4/1996 | Craig et al. | 623/20.11 |
| 5,545,228 A | 8/1996 | Kambin | |
| 5,549,682 A | 8/1996 | Roy | |
| 5,549,703 A | 8/1996 | Daigle et al. | |
| 5,556,433 A | 9/1996 | Gabriel et al. | |
| 5,569,263 A | 10/1996 | Hein | |
| 5,580,352 A | 12/1996 | Sekel | |
| 5,593,449 A | 1/1997 | Roberson, Jr. | |
| 5,613,970 A | 3/1997 | Houston et al. | |
| 5,702,457 A | 12/1997 | Walch et al. | |
| 5,743,918 A | 4/1998 | Calandruccio et al. | |
| 5,766,261 A * | 6/1998 | Neal et al. | 623/21.15 |
| 5,782,920 A | 7/1998 | Colleran | |
| 5,885,299 A | 3/1999 | Winslow et al. | |
| 5,902,340 A | 5/1999 | White et al. | |
| 5,906,644 A | 5/1999 | Powell | |
| 6,063,091 A | 5/2000 | Lombardo et al. | |
| 6,068,122 A | 5/2000 | Burns et al. | |
| 6,129,764 A | 10/2000 | Servidio | |
| 6,146,424 A | 11/2000 | Gray, Jr. et al. | |
| 6,149,687 A | 11/2000 | Gray, Jr. et al. | |
| 6,162,255 A | 12/2000 | Oyola | |
| 6,171,342 B1 | 1/2001 | O'Neil et al. | |
| 6,197,063 B1 * | 3/2001 | Dews | 623/19.14 |
| 6,214,052 B1 | 4/2001 | Burkinshaw | |
| 6,228,120 B1 | 5/2001 | Leonard et al. | |
| 6,423,096 B1 | 7/2002 | Musset et al. | |

OTHER PUBLICATIONS

McCormack, Damian, "Mechanical Axis Deviation: Definitions, Measurements and Consequences," http://www.iol.ie/~rcsiorth/journal/volume2/issue5/mech.htm (Aug. 30, 2000).

Hicks, *CORR*, vol. 321:111–116 (1995).

Ries, *J. Arthr.*, 13(1) (1998).

Stryker Howmedica Osteonics Total Knee Arthroplasty Total Stabilizer, http://www.osteonics.com/osteonics/knees/tsknee/tib.html (Feb. 17, 2000), page. 1.

Stryker Howmedica Osteonics Total Knee Arthroplasty Total Stabilizer, http://www.osteonics.com/osteonics/knees/tsknee/fem.html (Feb. 17, 2000), page. 1.

Tornier Brochure entitled "Prothese D'Epaule Aequalis Implant Humeral en Traumatologie" (undated).

Smith & Nephew Orthopaedics—Performance. Innovation. Trust. Brochure entitled "Neer II™ total shoulder system" (2000).

Smith & Nephew Orthopaedcs—Performance. Innovation. Trust. Brochure entitled "ideas in motion Modular Shoulder System" (2000).

Smith & Nephew Brochure entitled "Cofield$^2$ Total Shoulder System—Surgical Technique" pp. 1–32 (May 1997).

Smith & Nephew Brochure entitled "Cofield$^2$ Total Shoulder System Making a Posititve Impact on Shoulder Replacement" (Nov. 1996).

Smith & Nephew Brochure entitled "An Accurate, Reproducible, and Simple Solution to Complex Surgery Cofield$^2$ Total Shoulder System" pp. 1–22 (Dec. 1998).

* cited by examiner

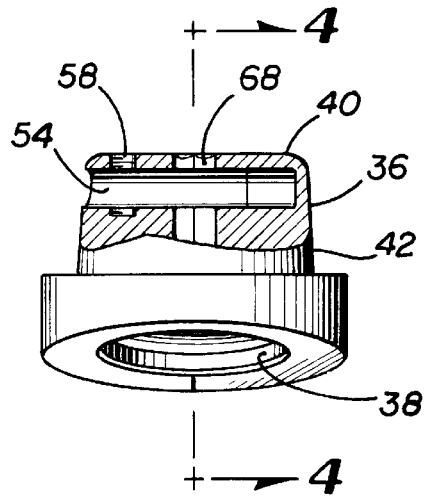 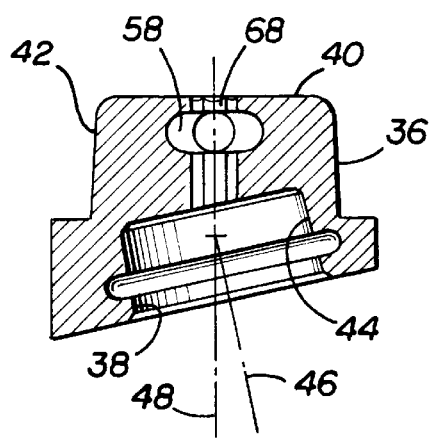
FIG 3  FIG 4
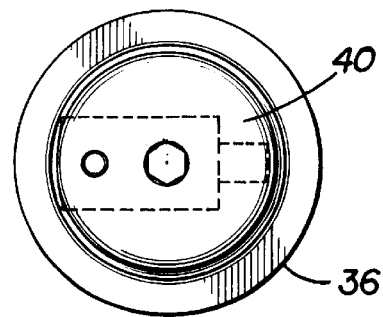
FIG 5
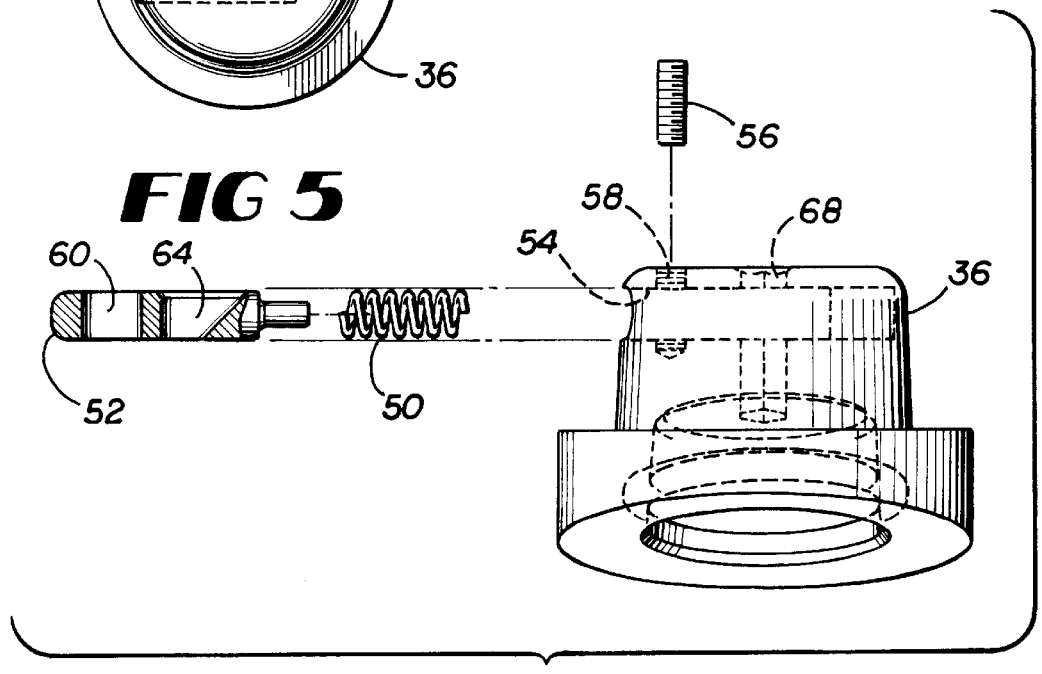
FIG 6

MULTI MODULAR TRIALING SYSTEM AND INSTRUMENTATION

RELATED APPLICATIONS

This application claims priority to Provisional Application No. 60/201,503 filed May 3, 2000 entitled, "Multi Modular Trialing System," which is incorporated by reference herein.

FIELD OF THE INVENTION

This invention relates generally to methods, instrumentation and devices for humeral implant positioning and more particularly to an improved trialing system utilizing an adjustment instrument and orientation indicia.

BACKGROUND OF THE INVENTION

The shoulder is one of the most complex joints in the body. Proper treatment of shoulder disorders and conditions involves solving many complex issues to achieve optimal clinical results. During a shoulder replacement operation, at least a portion of the proximal section of the humeral shaft will be replaced by a metal prosthesis. This prosthesis will generally consist of two parts: a stem that is mounted into the medullary canal of the humerus and a head component connected in some manner to the stem. The head component replaces the bearing surface of the humerus and articulates with the surface of the glenoid to allow the movement of the shoulder.

The stem and head components of a humeral prosthesis may be supplied in "modular" form, that is, as separate connectable components. Different stem sizes and head sizes in a modular implant design provide the surgeon with some degree of flexibility, which facilitates reconstruction of the original anatomy of the patient.

With a range of stem sizes and a range of head sizes available, the surgeon can choose a particular combination to suit the anatomy of each individual patient without having a large inventory of "integral" or "unitary" humeral prostheses. As used herein, "integral" and "unitary" mean formed in one continuous piece in contrast to the separate connectable components of a modular prosthesis. For example, one patient may require a relatively small head and a relatively long stem. With a unitary prosthesis, a wide range of stem lengths and diameters are required for each head size, whereas with a modular arrangement, a particular head may be used with a range of stem sizes, and a particular stem may be used with a variety of head sizes.

Additional variations also arise because individual patients may require differing angles of inclination of the head relative to the stem and differing eccentricities between the axis of the head and the axis of the stem. Thus, for example, in one patient, the eccentricity may be posterior and in another patient, it may be anterior. A modular shoulder prosthesis is disclosed in U.S. Pat. No. 6,197,063 B1, the entirety of which is hereby incorporated by reference.

Currently, humeral stem positioning does not provide for recordation of orientation of trials while allowing adjustment of inclination, head diameter, offset, eccentricity and version of the humeral head with respect to the humeral stem in situ.

SUMMARY OF THE INVENTION

Methods, devices and instrumentation of this invention seek to allow variable or incremental adjustment of inclination, diameter, offset, eccentricity and version in situ and recordation of these positions utilizing adjustment instrumentation and trials. Variable adjustment of inclination and version is possible without reliance on extensive use of interchangeable components. Accurate recordation of positioning is also possible, so that optimal positioning of the implant may be reproduced.

Methods, devices and instrumentation of this invention seek to provide a modular prosthesis in which a humeral head component, chosen to suit a patient, is attached to a stem chosen to suit the resected humerus of the patient using an intermediate connecting component. A set of prostheses is able to accommodate a wide range of variation, in a relatively inexpensive manner, by providing many of the variations required in the intermediate connecting component rather than in the more expensive humeral head.

Methods, devices and instrumentation of this invention utilize a series of trial intermediate connecting components which may be any one or a combination of offset, eccentric and angled and which mate with eccentric or non-eccentric humeral heads of various diameters and thicknesses. The trial intermediate connecting components and heads include structure corresponding to structure of an adjustment instrument according to this invention, so that the trial intermediate connecting components and heads may be adjusted either as one unit or independently. Adjustments in the inclination, offset, diameter, eccentricity and version of the humeral head is allowed. The design of the trials and instrumentation is such that the inclination, version, diameter, eccentricity and offset may be adjusted in situ. The instrumentation and trials also include features that indicate the relationship between the components, including the relationship between the head and the intermediate connecting component, as well as the relationship between the assembly of the head and intermediate connecting component and the humeral stem.

As used herein, component refers to any of the parts of a humeral prosthesis or trialing system. A modular humeral prosthesis or modular trailing system according to this invention generally comprises a stem to be fitted to a resected humerus, a head sized and configured to approximate the humeral head, and interconnecting component which may, but need not, take the form of an intermediate connecting component for connecting the stem to the head. Such an intermediate connecting component can include a first connector or connecting surface for connecting the intermediate connecting component to the stem, and a second connector or connecting surface for connecting the intermediate connecting component to the head. The first and second connectors on different intermediate connecting components may be disposed at different angles, and they may or may not have offsets relative to each other, in order to allow the surgeon a range of options in orienting the head of the prosthesis relative to the stem and the humerus.

While the surgeon will still need a traditional range of head sizes and stem sizes and lengths, the surgeon does not need additional heads or stems to provide a particular orientation of the head or a particular offset for the head. Thus, although a range of intermediate connecting components are required to be available to choose particular offsets and orientations, those intermediate connecting components are relatively inexpensive and less in number when compared with the high cost of the highly sophisticated head component, and the quantity of humeral heads that are required to provide the same degree of intraoperative flexibility.

In addition, the surgeon is able to choose the component parts independently of one another. Thus, the surgeon does not have to be concerned with questions of offset and orientation when selecting the correct head size and eccentricity. The same is true with regard to the stem, the surgeon can choose the correct stem to fit the medullary canal in the humerus, thus providing a long lasting and secure joint between the stem and the bone. Having selected these components, the surgeon can independently decide on the particular offset and orientation of the head relative to the stem and select an intermediate connecting component accordingly. The surgeon is, therefore, able to match the modular prosthesis used to the original anatomy of a particular patient with respect to the current position and soft tissue structures. Having matched the trialing head and connecting component and having obtained optimal positioning using the adjustment instrument of this invention, the surgeon may then utilize indicia provided to record the desired position, and repeat this positioning in the actual implant.

One feature of this invention is the ability to readjust version, inclination and eccentricity in situ without removal of the head or stem.

Another feature of this invention is the ability to use an adjustment instrument easily to adjust position or orientation of the intermediate connecting component, the humeral head, or both.

Another feature of this invention is the ability to read indicia directly in order to match or replicate the positioning or orientation of the implant exactly to the position of the trial.

Another feature of this invention is readjustment of positioning or orientation without a loosening and tightening of the trial portions and with reference to prior positioning of the trials.

Another feature of this invention is the ability to adjust inclination, version and eccentricity, or any combination thereof, simultaneously without being required to interchange components to adjust each individual aspect of the humeral head position.

These and other features of this invention will become apparent from the drawings and description below.

BRIEF DESCRIPTION OF THE DRAWINGS

FIG. 3 is a side view in partial cross section of one form of interconnecting component, in this case, an intermediate connecting component, according to one embodiment of this invention.

FIG. 4 is a side view in cross-section of the intermediate connecting component of FIG. 3.

FIG. 5 is an end view of the intermediate connecting component of FIG. 3.

FIG. 6 is an exploded perspective view of a locking mechanism and an intermediate connecting component of another embodiment of this invention.

DETAILED DESCRIPTION

Methods, devices and instrumentation according to this invention seek to provide a modular humeral prosthesis, including a stem that is adapted to be fitted to a resected humerus, a head that is adapted to approximate the size and shape of a humeral head, an interconnecting component, such as an intermediate connecting component, for connecting the stem to the head, an adjustment instrument for adjusting orientation of the prosthesis in situ, and devices for indicating trialing orientation. FIGS. 1–8 and 13–16 show components to illustrate not only actual protheses or portions of prostheses that can be implanted in patients, but also trial components that can be used in accordance with this invention. Where circumstances are appropriate, this disclosure mentions whether the components referred to are actual prosthesis components or trial components.

Adjustment of the center of rotation of the humeral head relative to the shaft, as well as adjustment of one of a set of intermediate connecting components, is provided in order to allow adjustment of diameter, offset, version, inclination, and eccentricity. Devices for indicating trailing orientation are provided for recreation of trailing orientation on the actual implant components. In one embodiment, indicia on the trial components match indicia on the actual implant. Trial components are utilized together with an instrument for adjusting inclination, version and eccentricity. In one embodiment, a trial humeral head and a trial intermediate connecting component are utilized together with an instrument for adjusting inclination, version and eccentricity.

Figures 1, 2:
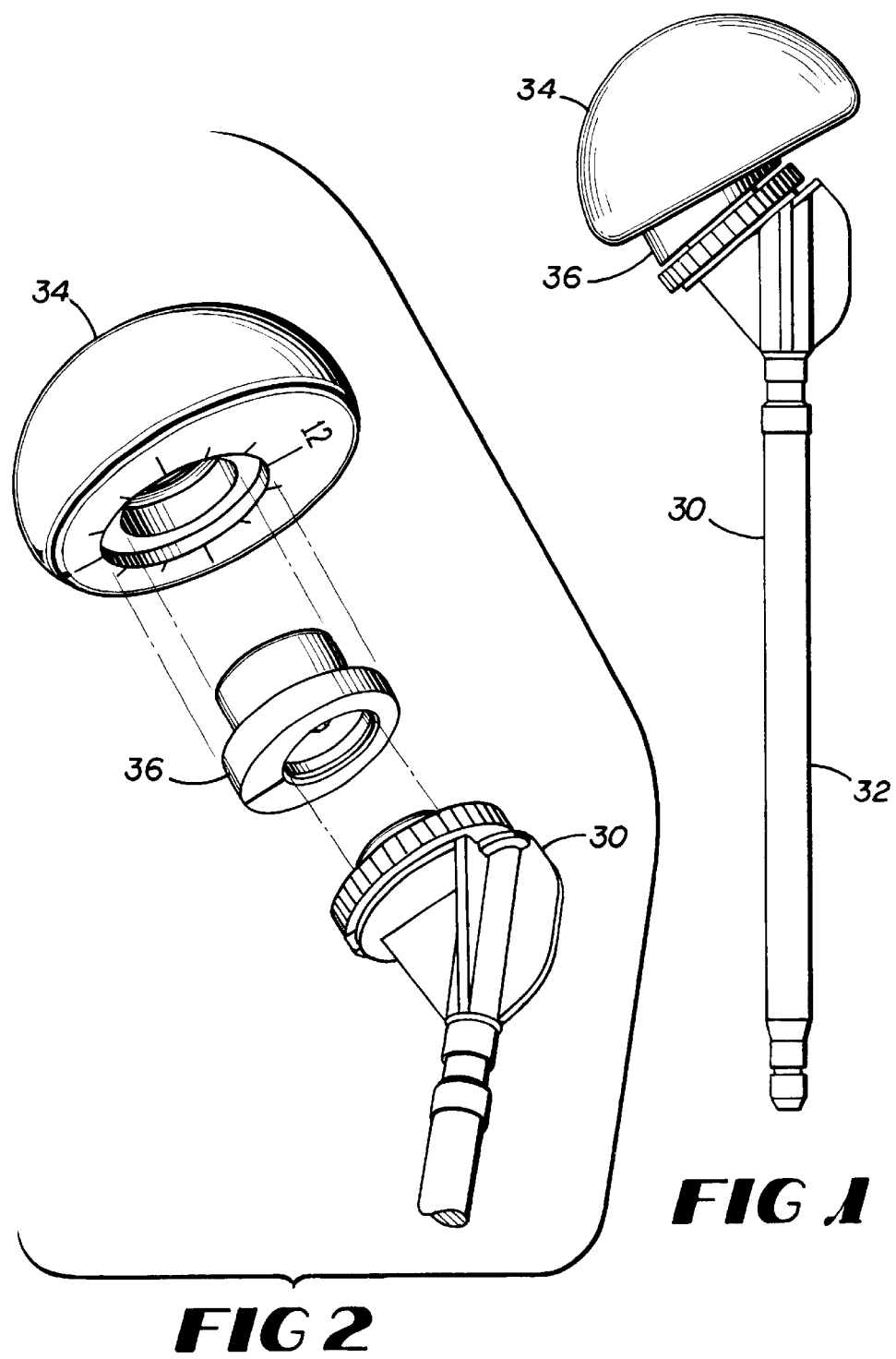
FIG. 1 is a side view of a modular humeral prosthesis according to one embodiment of this invention.
FIG. 2 is an exploded perspective view of the prosthesis of FIG. 1.

Consider one example of instrumentation and devices according to this invention. Stem component 30, shown in FIGS. 1 and 2, is available in a number of different diameters and lengths to match the size to which the medullary canal (not shown) has been reamed or broached. Shaft 32 of stem 30 is designed to contact the previously reamed or broached medullary canal and extend into the remaining humerus to prevent any movement of stem 30.

Humeral head component 34, also shown in FIGS. 1 and 2, is designed to articulate with the scapula or glenoid prosthesis (not shown). Head 34 replaces the articulating surface of the humerus and is largely hemispherical in shape. A variety of sizes of humeral heads are provided to complement the patient's scapula or glenoid prosthesis and soft tissue balance. The articulating surface of implant head 34 may be highly polished to reduce friction, which reduces wear on the scapula or glenoid prosthesis.

In one embodiment, the position of head 34 may be varied by using different intermediate connecting components 36, shown in FIGS. 1–5, as are appropriate in each individual case. There can be a large variety in the shape, size and orientation of human humeral bones and therefore it is desirable to tailor the humeral prosthesis to suit each individual case. Various designs of intermediate connecting components provide a massive range of different head positions and orientations relative to the humeral stem that can be selected and connected interoperatively.

One embodiment of intermediate connecting component 36 is shown in FIGS. 3, 4 and 5. Intermediate connecting component 36 has first connector 38, which is formed as a surface of rotation and adapted to cooperate with stem 30 in order to mount intermediate connecting component 36 to stem 30, and also has second connector 40, which is formed as a surface of rotation and adapted to cooperate with head 34 in order to mount head 34 to intermediate connecting component 36. In one embodiment, second connector 40 includes a self-locking tapered surface 42. Preferably, first connector 38 is a cavity formed in second connector 40 adapted at least partially to receive a projection of stem 30 and features a self-locking tapered surface 44. More particularly, tapered surfaces 42, 44 are of the "Morse taper" type. A Morse taper forms an angle, providing a self-locking function. In other words, when two corresponding Morse tapers are pushed together using an external force, they tend to remain mated.

Alternatives to a Morse taper include other suitable locking tapers, as well as any mating conditions that would include a male and female surface, such as, but not limited to, a ball and socket. For purposes of trialing, the Morse tapers do not necessarily have to lock together. As a result, the trial components may utilize any feature or features that allow the trial head to rotate about the intermediate connecting component and allow the intermediate connecting component to rotate about the stem. In an alternative embodiment, a first connector is adapted to be at least partially received in a cavity of stem 30. A second connector is a cavity formed in the first connector and adapted at least partially to receive a projection on head 34. In another embodiment, intermediate connecting component 36 may consist of two male tapers or two female tapers. In an alternative embodiment, the mating of head 34 and intermediate connecting component 36, and the mating of stem 30 and intermediate connecting component 36, does not include tapers. In another embodiment, the first and second connectors have different mating surfaces. For example, the first connector may comprise a taper, while the second connector comprises a sphere. Many combinations of mating surfaces are possible.

For trialing purposes, intermediate connecting component 36 need not be a separate component. In one embodiment, intermediate connecting component 36 is permanently attached to head 34 or stem 30. For example, the assembly of head 34 and intermediate connecting component 36 may be a one-piece design consisting of multiple components that move in a similar manner to the two-piece design of the above described embodiment.

As shown in FIG. 4, second connector 40 is inclined at an angle relative to first connector 38. First connector 38 has axis 46, and second connector 40 has axis 48, each of which axes 46, 48 are offset from each other in order to cause first connector 38 to be offset from second connector 40. Other intermediate connecting components may be provided in which the surfaces of rotation of each of the first and second connectors share the same axis of rotation, in which the surfaces are generally parallel to each other but offset, or in which the surfaces are inclined at an angle relative to each other, causing the first and second connectors to be inclined at an angle relative to each other. In another embodiment, the intermediate connecting component has first and second connectors that are eccentric. Further, any combination of offset, angled, or eccentric connectors may be used in a particular embodiment.

In a preferred embodiment, intermediate connecting component 36 is adapted to rotate 360 degrees relative to each of stem 30 and head 34. In this embodiment, shown in FIG. 4, first connector 38 and second connector 40 are generally circular in cross section.

In one embodiment, shown in FIG. 6, trial intermediate connecting component 36 is coupled to trial head 34 (not shown) with a locking mechanism so that they may be removed as one unit. This locking mechanism may be any suitable locking mechanism. In the embodiment shown in FIG. 6, the locking mechanism is a plate detent. Spring 50 is mated to plunger 52, and then the plunger 52 and spring 50 are inserted into cavity 54. Rod 56 slides into rod aperture 58, and through slot 60 in plunger 52, holding plunger 52 in cavity 54. Upon insertion of an adjustment instrument of this invention in aperture 68 of intermediate connecting component 36, an engaging hex on the adjustment instrument enters plunger aperture 64, pulling back the locking mechanism, thus allowing movement of the intermediate connecting component 36, head 34, or both.

In an alternative embodiment, the locking mechanism is not integral to the intermediate connecting component. In one embodiment, the locking mechanism is on the humeral head, and the groove is on the intermediate connecting component. Locking the intermediate connecting component to the head may also be accomplished using a set-screw, ball plunger, or other suitable locking mechanism that allows the head and intermediate connecting component to be removed from the stem as one unit, so the relationship between the two may be recorded. In addition, the locking mechanism prevents the head from spinning about the intermediate connecting component. This locking function is necessary to maintain the position of the head and intermediate connecting component during the trial range of motion. In an alternative embodiment, multiple locking mechanisms are utilized.

Figure 7:
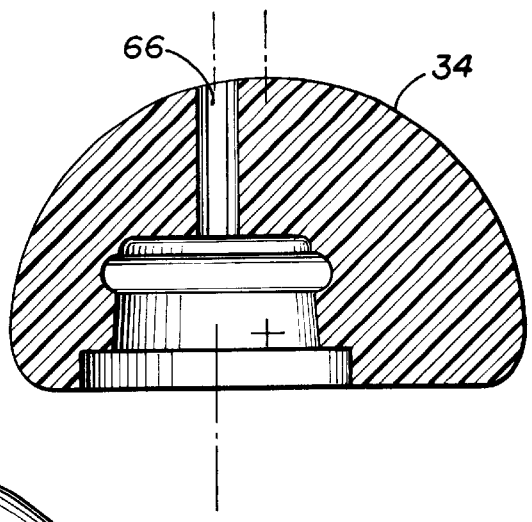
FIG. 7 is a side cross sectional view of one form of humeral head according to one embodiment of this invention.
Figure 8:
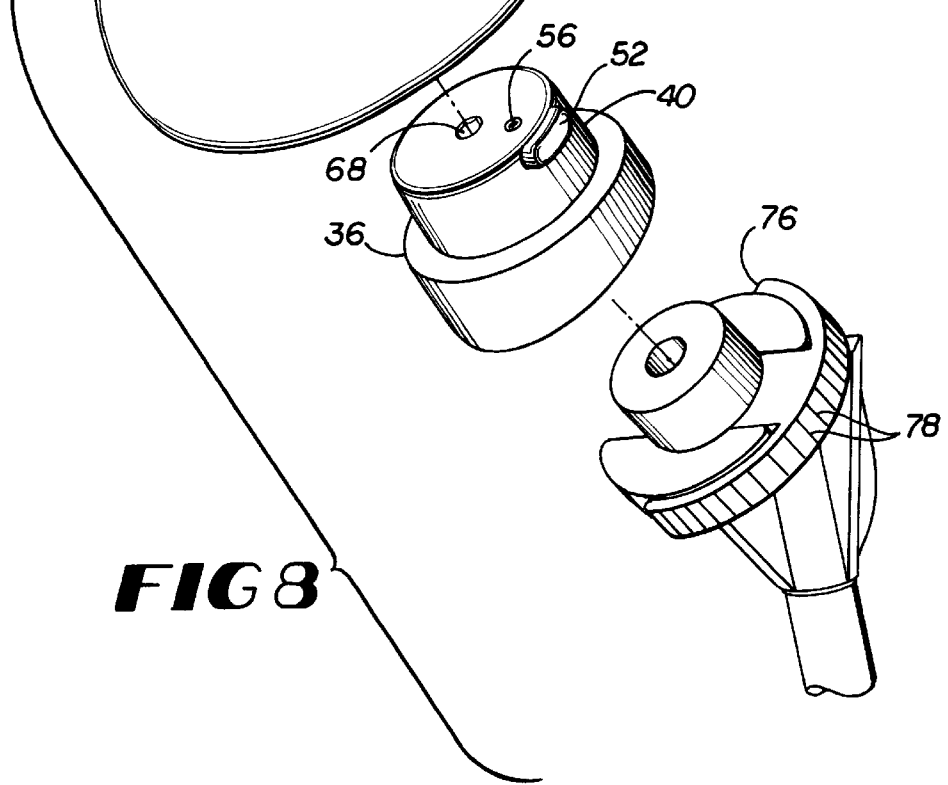
FIG. 8 is a partial, exploded, perspective view of one form of a modular humeral prosthesis according to one embodiment of this invention.
Figures 10, 11, 12:
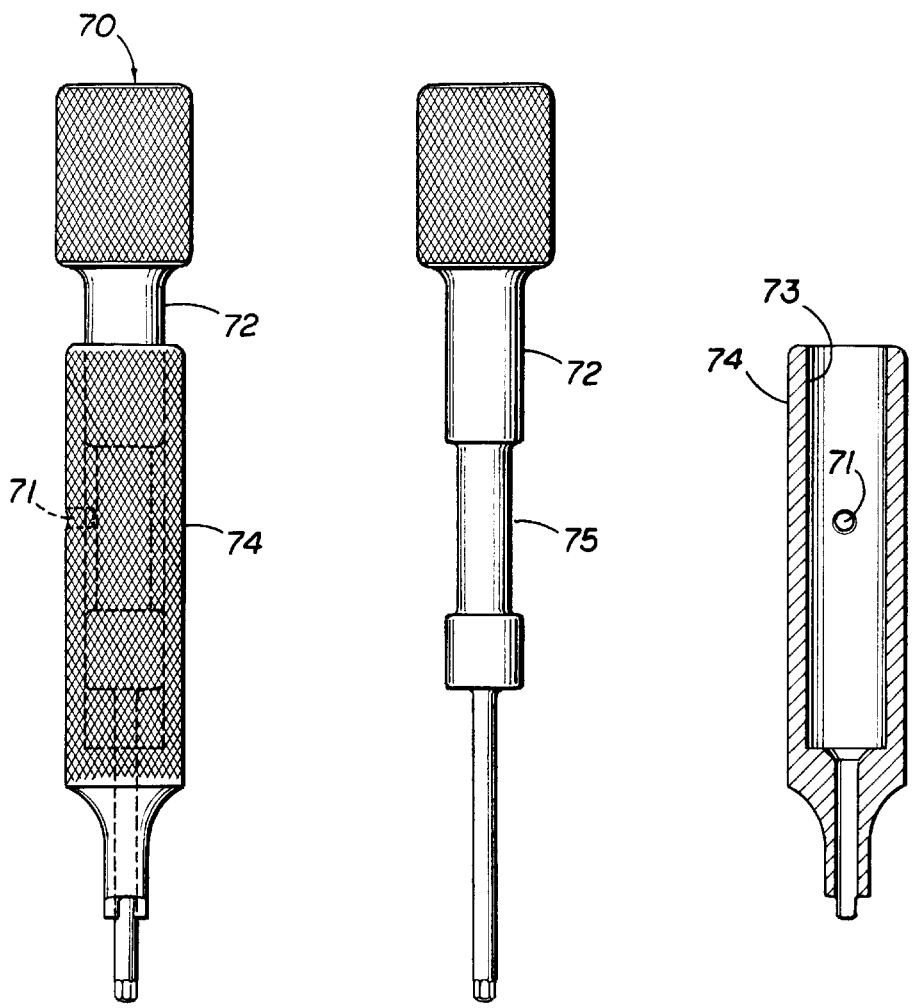
FIG. 10 is a side view in partial cross section of the adjustment instrument of FIG. 9.
FIG. 11 is a side view of the inner portion of the adjustment instrument of FIG. 9.
FIG. 12 is a side view in cross section of the outer portion of the adjustment instrument of FIG. 9.
Figure 9:
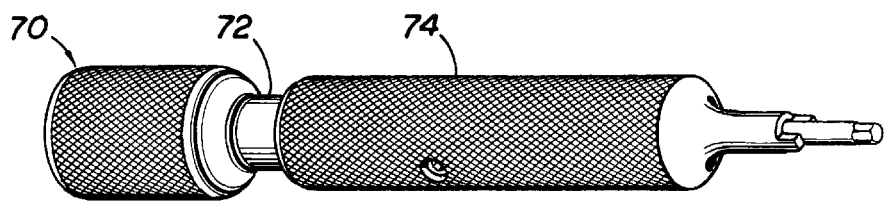
FIG. 9 is a perspective view of one form of an adjustment instrument according to one embodiment of this invention.

Trial humeral head 34 includes aperture 66, shown in FIGS. 7 and 8. Trial head aperture 66 of trial head 34 has corresponding structure to the structure of an adjustment instrument of this invention, so that one structure drives the rotation of the other structure. Intermediate connecting component 36 also has structure that corresponds to the structure of an adjustment instrument. The corresponding structure of trial head 34 and intermediate connecting component 36 may be any suitable structure or mechanism that allows rotational resistance between the adjustment instrument and the trial, such as mating structures and keyed structures. Such structures and mechanisms may include, but are not limited to, square drives, hex drives, torx drives, and racks and pinions. In a more specific embodiment, shown in FIG. 8, intermediate connecting component 36 has a hex drive opening 68, located along the centerline of second connector 40, in order to provide rotational resistance between the adjustment instrument and trial head 34. In an alternative embodiment, the corresponding structure does not lie on the centerline of second connector 40 of intermediate connecting component 36.

Adjustment instrument 70, shown in FIGS. 9, 10, 11 and 12, has an inner interface or portion 72 that has corresponding structure to trial intermediate connecting component 36, and an outer portion 74 that has corresponding structure to trial humeral head 34, so that one structure drives the rotation of the other structure, as described above. Inner and outer portions 72, 74 of instrument 70 may be secured together to prevent separation. In a particular embodiment, shown in FIGS. 9, 10, 11 and 12, portion 72 is located rotatably in, and generally coaxial to, portion 74. In this embodiment, inner and outer portions 72, 74 are secured with pin 71, which may be welded to outer portion 74, extends beyond inner wall 73 of outer portion 74 and is positioned to "ride" in groove 75 located on inner portion 72 (see FIG. 11). Other structures which will be evident to persons in this field may just as easily be employed. For instance, inner and outer portions 72, 74 may also be secured with a variety of retaining rings, or any other retaining structure. Securing inner and outer portions 72, 74 together is a matter of convenience and is not critical to the function of adjustment instrument 70.

Inner and outer portions 72, 74 are able, in one embodiment, to rotate either independently of each other, or together as one unit. Inner portion 72 is also allowed to translate within outer portion 74 a specified distance. This translation allows adjustment instrument 70 to engage intermediate connecting component 36 independent of humeral head 34, or to engage humeral head 34 independent of intermediate connecting component 36; or it is possible to engage both at the same time. Inner portion 72 engages intermediate connecting component 36 and outer portion 74 engages humeral head 34. In an alternative embodiment, the outer portion engages the intermediate connecting component and the inner portion engages the humeral head.

Figures 13, 14:
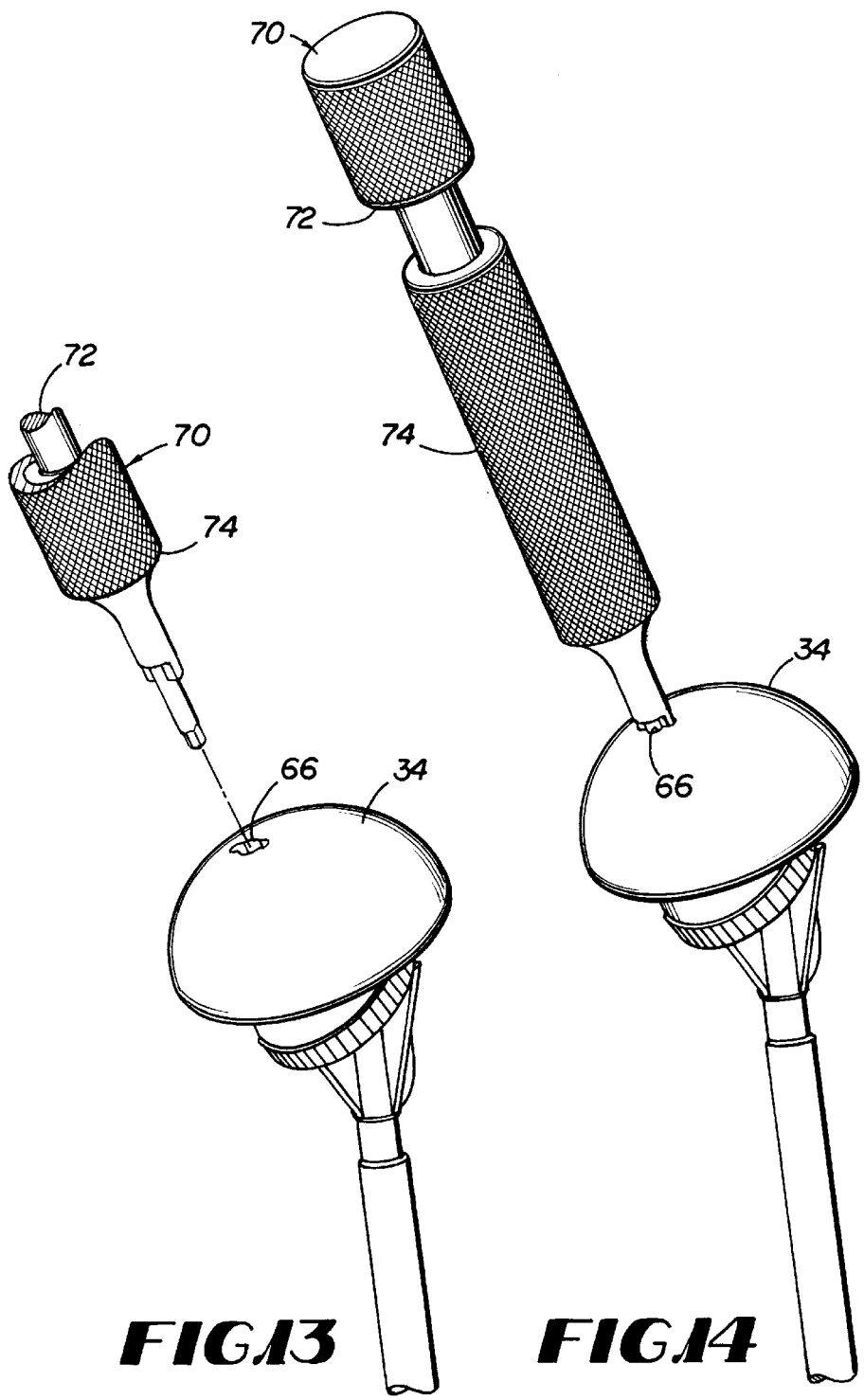
FIG. 13 is an exploded, partial, perspective view of one form of an adjustment instrument and modular humeral prosthesis according to one embodiment of this invention.
FIG. 14 is a perspective view of the instrument and prosthesis of FIG. 13.

Optimal orientation of head 34 and intermediate connecting component 36 may be achieved in situ, without removal of head 34 or intermediate connecting component 36, by using adjustment instrument 70. As shown in FIGS. 13 and 14, adjustment instrument 70 engages head 34 and intermediate connecting component 36, entering aperture 66. The surgeon is able to rotate either head 34, intermediate connecting component 36, or both, in order to obtain optimal inclination, eccentricity and version, among other parameters. By holding outer portion 74 stationary and rotating inner portion 72, for instance, intermediate connecting component 36 can be rotated or positioned independent of humeral head 34. By holding inner portion 72 stationary and rotating outer portion 74, head 34 can be rotated or positioned independent of intermediate connecting component 36. Rotating both inner and outer portions 72, 74 simultaneously will rotate or position intermediate connecting component 36 and head 34 relative to stem 30. Positioning of the trial components independently, or in combination, provides the opportunity to adjust inclination, version and eccentricity, among other parameters, and to note such adjustments, in order to replicate them on the actual implants for optimal reconstruction of the anatomy.

Figures 15, 16:
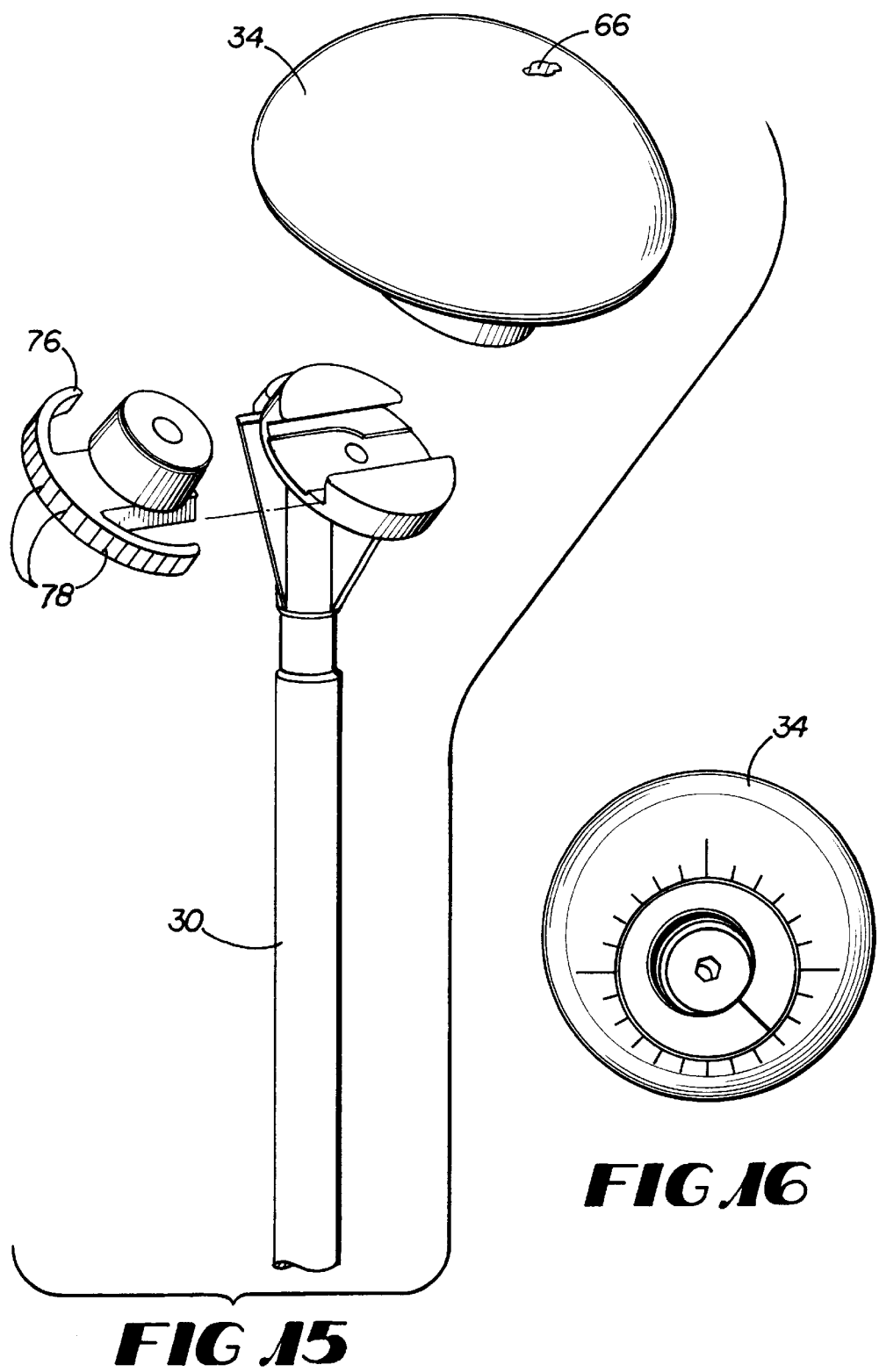
FIG. 15 is an exploded perspective view of one form of a modular humeral prosthesis according to one embodiment of this invention.
FIG. 16 is an end view of one form of a humeral head and intermediate connecting component according to one embodiment of this invention.

In one embodiment shown in FIGS. 8 and 15, coupling member 76 is attached to stem 30 and rotationally constrained. Coupling member 76 includes indicia 78, such as calibrated marks created by a laser. Other suitable indicia, such as mill-etch detail, may also be used. Upon achievement of the desired orientation, these indicia are used to indicate the relationship between the assembly of head 34 and intermediate connecting component 36 and the humeral stem 30. After the desired orientation is determined, the relationship between head 34 and intermediate connecting component 36 is indicated by indicia, such as a calibrated laser mark, on the bottom of the assembly of humeral head 34 and intermediate connecting component 36, as shown in FIG. 16. In a preferred embodiment, shown in FIG. 1, the indicia are equally spaced and include a number 12 oriented to provide a reference, similar to the face of a clock. This relationship between trial head 34 and trial intermediate connecting component 36 may be replicated between the actual implant head and the implant intermediate connecting component by reference to indicia on these implant structures. The relationship between these two trial components and humeral stem 30 also may be replicated by replicating the assembly of these two trial components relative to the humeral stem 30.

In an alternative embodiment, the relationship between trial intermediate connecting component 36 and stem 30 is determined and replicated between the actual implant intermediate connecting component and stem. Subsequently, the relationship between this intermediate connecting component and stem construct and the trial humeral head is determined and replicated between the actual implant head and intermediate connecting component. In an alternative embodiment, the indicia are located directly on the stem, and a coupling member is not required.

In an alternative embodiment, adjustment instrument 70 indicates the relationship between the assembly of head 34 and intermediate connecting component 36, and stem 30. In an alternative embodiment, the relationships may be recorded and read from the instrument itself. For example, in one alternative embodiment, adjustment instrument 70 is a three-piece design that allows the user to record the relationship between the head and intermediate connecting component and the relationship between the head or intermediate connecting component and the stem. This device requires that all the trial components have appropriate corresponding structure in such a manner to allow the instrument to be used properly. In one embodiment, the inner portion of the instrument has structure corresponding to structure of the stem, the intermediate portion of the instrument has structure corresponding to structure of the intermediate connecting component and the outer portion of the instrument has structure corresponding to structure of the humeral head. Each portion has structure that permits the relationship between components to be measured. The relationship is measured utilizing calibrated laser marks, etched lines, or other suitable indicia located on the shaft of each portion of the instrument.

One method of using one form of structure according to this invention, which includes a humeral head, stem and intermediate connecting component, for obtaining and recording optimal positioning is as follows:

1. Resect the proximal end of a humerus to remove the head and prepare the medullary canal to receive the stem.
2. Place trial stem in humerus.
3. Utilize an intermediate connecting component to connect the trial stem to the humeral head.
4. Utilize an adjustment instrument to approximate version and inclination.
5. Engage an appropriate trial head with the intermediate connecting component.
6. Utilize an adjustment instrument to adjust head center position.
7. Perform a trial range of motion.
8. Assess the stability of the shoulder.
9. Adjust any one or combination of the inclination, version and eccentricity, or replace any one or combination of intermediate connecting component, head or stem, and repeat steps 2–8.

10. Note sizes of intermediate connecting component, head and stem.
11. Note relative positions of the intermediate connecting component and either the head, stem or both.
12. Match implant geometry and positioning to positioning of other trial components, and repeat positioning on actual implants.

Another method of using one form of structure according to this invention, which includes a humeral head, stem and intermediate connecting component, for obtaining and recording optimal positioning is as follows:

1. Resect the proximal end of a humerus to remove the head and prepare the medullary canal to receive the stem.
2. Place trial stem in humerus and engage coupling member.
3. Place the intermediate connecting component on the coupling member on the stem.
4. Using the adjustment instrument, adjust the intermediate connecting component to approximate version and inclination.
5. Place the appropriate trial head on the intermediate connecting component.
6. Using the adjustment instrument, place the head at the appropriate head center position.
7. Perform a trial range of motion.
8. Assess the stability of the shoulder.
9. Adjust one or combination of the inclination, version or head center eccentric position using the adjustment instrument, or replace any one or combination of intermediate connecting component, head, or stem, and repeat steps 2–8.
10. Note the intermediate connecting component, size humeral head, position of the head and intermediate connecting component assembly to the stem collar and the position of the intermediate connecting component to the head and the stem size.
11. Match implant geometry and positioning to positioning of other trial components, and repeat positioning on actual implants.

Similar instrumentation and trials may be used in other areas, such as any with spherical or hinge articulation, including, but not limited to, a hipjoint or a finger joint.

As various changes could be made in the above constructions and methods without departing from the scope of the invention as defined in the claims, it is intended that all matter contained in the above description or shown in the accompanying drawings be interpreted as illustrative and not in a limiting sense.

What is claimed is:

1. A modular trialing system for use in replacement of the humeral head of a humerus, comprising:
    (a) a stem component adapted to be fitted to a resected humerus;
    (b) a trial head component not suitable for actual implantation into a patient as an orthopedic implant and adapted to approximate the size and shape of a humeral head;
    (c) an intermediate connecting component for connecting the stem to the head; and
    (d) at least one set of indicia adapted to indicate positioning of at least one component relative to at least one of the other components, in which the indicia correspond to indicia on prosthesis components to allow positioning of the prosthesis components to correspond to positioning of trial components when placed in the body.

2. A system according to claim 1 in which the intermediate connecting component comprises:
    (a) a first connector that is formed as a surface of rotation and adapted to cooperate with the stem in order to mount the intermediate connecting component to the stem; and
    (b) a second connector that is formed as a surface of rotation and adapted to cooperate with the head in order to mount the head to the intermediate connecting component.

3. A system according to claim 2 in which the second connector includes a self-locking tapered surface.

4. A system according to claim 2 in which the first connector is adapted to be at least partially received in a cavity of the stem and features a self-locking tapered surface.

5. A system according to claim 2 in which the first connector is a cavity formed in the second connector and adapted at least partially to receive a projection that projects from the stem.

6. A system according to claim 2 in which the second connector is a cavity formed in the first connector and adapted at least partially to receive a projection that projects from the head.

7. A system according to claim 2 in which the intermediate connecting component is adapted to rotate 360 degrees relative to each of the stem and the head.

8. A system according to claim 2 in which the second connector is inclined at an angle relative to the first connector.

9. A system according to claim 2 in which each of the first connector and second connector have an axis, and in which said axes are offset from each other in order to cause the first connector to be offset from the second connector.

10. A system according to claim 1 in which the at least one set of indicia is adapted to indicate positioning of the head relative to the intermediate connecting component.

11. A system according to claim 1 in which the at least one set of indicia is adapted to indicate positioning of the intermediate connecting component relative to the stem.

12. A system according to claim 1 in which the at least one set of indicia is adapted to indicate positioning of an assembly of the head and intermediate connecting component relative to the stem.

13. A system according to claim 1 in which the at least one set of indicia is adapted to indicate positioning of an assembly of the stem and intermediate connecting component relative to the head.

14. A system according to claim 1 in which the at least one set of indicia is on a bottom face of the head.

15. A system according to claim 1 in which the at least one set of indicia is on the second connector.

16. A system according to claim 1 in which the at least one set of indicia is on the first connector.

17. A system according to claim 1 in which the at least one set of indicia is on the stem.

18. A system according to claim 1 further comprising a coupling member adapted to cooperate with the intermediate connecting component and the stem, in which the at least one set of indicia is on the coupling member.

19. A system according to claim 1 in which the indicia are calibrated laser marks.

20. A system according to claim 1 in which the intermediate connecting component and the head are coupled and removable from the stem as one component.

21. A system according to claim 20 in which the head and intermediate connecting component are coupled using a plate detent.

22. A system according to claim 20 in which the coupling prevents the head from rotating relative to the intermediate connecting component.

23. A system according to claim 1 further comprising an instrument comprising a first interface and a second interface, in which the head and intermediate connecting component are adapted to receive the instrument.

24. A system according to claim 23 in which the intermediate connecting component engages the first interface of the instrument, and the head engages the second interface of the instrument.

25. A system according to claim 23 in which the first interface and the second interface of the instrument rotate independently of each other and as one unit.

26. A system according to claim 23 in which the first and second interfaces are generally coaxial.

27. A system according to claim 23 in which one of the first and second interfaces translates within the other of the first and second interfaces, allowing independent engagement of one of the intermediate connecting component and head.

28. A system according to claim 23 in which one of the first and second interfaces translates within the other of the first and second interfaces, allowing engagement of both of the intermediate connecting component and head.

29. A system according to claim 23 in which the intermediate connecting component is adapted to provide rotational resistance between the intermediate connecting component and the instrument.

30. A system according to claim 23 in which the head is adapted to provide rotational resistance between the head and the instrument.

31. A system according to claim 23 in which the orientation of the head and intermediate connecting component may be adjusted in situ.

32. A modular trialing system for replacement of the humeral head of a humerus, comprising:
(a) a stem component adapted to be fitted to a resected humerus;
(b) a trial head component not suitable for actual implantation into a patient as an orthopedic implant and adapted to approximate the size and shape of a humeral head, the head featuring a bottom face;
(c) an intermediate connecting component for connecting the stem to the head, the intermediate connecting component including:
a first connector adapted to cooperate with the stem component to mount the stem to the intermediate connecting component, the first connector generally circular in cross section and including a self locking taper; and
a second connector adapted to cooperate with the head component to mount the head to the intermediate connecting component, the second connector generally circular in cross section and including a self locking taper that is adapted to mount the intermediate connecting component to the head;
(d) at least one set of indicia, adapted to indicate positioning of at least one component relative to at least one of the other components, in which the indicia correspond to indicia on prosthesis components to allow positioning of the prosthesis components to correspond to positioning of trial components when placed in the body; and
(e) an instrument for adjusting positioning of the components.

33. A system according to claim 32 in which the first connector is a male component adapted to be received at least partially in a cavity in the stem.

34. A system according to claim 32 in which the second connector is a male component adapted to be received at least partially in a cavity in the head.

35. A system according to claim 32 in which the at least one set of indicia is adapted to indicate positioning of the head relative to the intermediate connecting component.

36. A system according to claim 32 in which the at least one set of indicia is adapted to indicate positioning of the intermediate connecting component relative to the stem.

37. A system according to claim 32 in which the at least one set of indicia is adapted to indicate positioning of an assembly of the head and intermediate connecting component relative to the stem.

38. A system according to claim 32 in which the at least one set of indicia is adapted to indicate positioning of an assembly of the stem and intermediate connecting component relative to the head.

39. A system according to claim 32 in which the at least one set of indicia is on a bottom face of the head.

40. A system according to claim 32 in which the at least one set of indicia is on the second connector.

41. A system according to claim 32 in which the at least one set of indicia is on the first connector.

42. A system according to claim 32 in which the at least one set of indicia is on the stem.

43. A system according to claim 32 further comprising a coupling member adapted to cooperate with the intermediate connecting component and the stem, in which the at least one set of indicia is on the coupling member.

44. A system according to claim 32 in which the indicia are calibrated laser marks.

45. A system according to claim 32 in which the intermediate connecting component and the head are coupled and removable from the stem as one component.

46. A system according to claim 45 in which the head and intermediate connecting component are coupled using a plate detent.

47. A system according to claim 45 in which the coupling prevents the head from rotating relative to the intermediate connecting component.

48. A system according to claim 32 in which the instrument comprises:
(a) a first interface adapted to engage an intermediate connecting component; and
(b) a second interface adapted to engage a humeral head;
in which one of the first and second interfaces is rotatably mounted relative to the other of the first and second interfaces in order to allow at least one component to be adjusted relative to another component.

49. A system according to claim 48 in which the first interface and the second interface of the instrument rotate independently of each other and as one unit.

50. A system according to claim 48 in which the first and second interfaces are generally coaxial.

51. A system according to claim 48 in which one of the first and second interfaces translates within the other of the first and second interfaces, allowing independent engagement of one of the intermediate connecting component and head.

52. A system according to claim 48 in which one of the first and second interfaces translates within the other of the first and second interfaces, allowing engagement of both of the intermediate connecting component and head.

53. A system according to claim 48 in which the intermediate connecting component is adapted to provide rotational resistance between the intermediate connecting component and the instrument.

54. A system according to claim 48 in which the head is adapted to provide rotational resistance between the head and the instrument.

55. A system according to claim 48 in which the orientation of the head and intermediate connecting component may be adjusted in situ.

56. A modular humeral prosthesis for use in replacement of the humeral head of a humerus, comprising:
   (a) a stem component adapted to be fitted to a resected humerus;
   (b) a head component adapted to approximate the size and shape of a humeral head;
   (c) an intermediate connecting component for connecting the stem to the head and wherein the intermediate connecting component is adapted to rotate 360 degrees relative to each of the stem and the head; and
   (d) at least one set of indicia, adapted to indicate positioning of at least one component relative to at least one of the other components, in which the indicia are adapted to correspond to indicia on trial components in order to allow positioning of the prosthesis components to correspond to positioning of trial components when placed in the body, wherein the components may be positioned without removing the components from the humerus.

57. A system according to claim 56 in which the intermediate connecting component comprises:
   (a) a first connector that is formed as a surface of rotation and adapted to cooperate with the stem in order to mount the intermediate connecting component to the stern; and
   (b) a second connector that is formed as a surface of rotation and adapted to cooperate with the head in order to mount the head to the intermediate connecting component.

58. A system according to claim 57 in which the second connector includes a self-locking tapered surface.

59. A system according to claim 57 in which the first connector is adapted to be at least partially received in a cavity of the stem and features a self-locking tapered surface.

60. A system according to claim 57 in which the first connector is a cavity formed in the second connector and adapted at least partially to receive a projection that projects from the stem.

61. A system according to claim 57 in which the second connector is a cavity formed in the first connector and adapted at least partially to receive a projection that projects from the head.

62. A system according to claim 57 in which the second connector is inclined at angle relative to the first connector.

63. A system according to claim 57 in which each of the first connector and second connector have an axis, and in which said axes are offset from each other in order to cause the first connector to be offset from the second connector.

64. A system according to claim 56 in which the at least one set of indicia is adapted to indicate positioning of the head relative to the intermediate connecting component.

65. A system according to claim 56 in which the at least one set of indicia is adapted to indicate positioning of the intermediate connecting component relative to the stem.

66. A system according to claim 56 in which the at least one set of indicia is adapted to indicate positioning of an assembly of the head and intermediate connecting component relative to the stem.

67. A system according to claim 56 in which the at least one set of indicia is adapted to indicate positioning of an assembly of the stem and intermediate connecting component relative to the head.

68. A system according to claim 56 in which the at least one set of indicia is on a bottom face of the head.

69. A system according to claim 56 in which the at least one set of indicia is o the second connector.

70. A system according to claim 56 in which the at least one set of indicia is on the first connector.

71. A system according to claim 56 in which the at least one set of indicia is on the stem.

72. A system according to claim 56 further comprising a coupling member adapted to cooperate with the intermediate connecting component and the stem, in which the at least one set of indicia is on the coupling member.

73. A system according to claim 56 in which the indicia are calibrated laser marks.

74. A system according to claim 56 in which the intermediate connecting component and the head are coupled and removable from the stem as one component.

75. A system according to claim 56 in which the head and intermediate connecting component are coupled using a plate detent.

76. A system according to claim 56 in which the coupling prevents the head for rotating relative to the intermediate connecting component.

77. A system according to claim 56 further comprising an instrument comprising a first interface and a second interface, in which the head and intermediate connecting component are adapted to receive the instrument.

78. A system according to claim 77 in which the intermediate connecting component engages the first interface of the instrument, and the head engages the second interface of the instrument.

79. A system according to claim 77 in which the first interface and the second interface of the instrument rotate independent of each other and as one unit.

80. A system according to claim 77 which the first and second interfaces are generally coaxial.

81. A system according to claim 77 in which one of the first and second interfaces translates within the other of the first and second interfaces, allowing independent engagement of one of the intermediate connecting component and head.

82. A system according to claim 77 in which one of the first and second interfaces translates within the other of the first and second interfaces, allowing engagement of both of the intermediate connecting component and head.

83. A system according to claim 77 in which the intermediate connecting component is adapted to provide rotational resistance between the intermediate connecting component and the instrument.

84. A system according to claim 77 in the head is adapted to provide rotational resistance between the head and the instrument.

85. A system according to claim 77 in which the orientation of the head and intermediate connecting component may be adjusted in situ.

86. A modular humeral prosthesis for use in replacement of the humeral head of a humerus, comprising:
   (a) a stem component adapted to be fitted to a resected humerus;
   (b) a head component adapted to approximate the size and shape of a humeral head, the head featuring a bottom face;

(c) an intermediate connecting component for connecting the stem to the head, the intermediate connecting component including:
  a first connector adapted to cooperate with the stem component to mount the stern to the intermediate connecting component, the first connector generally circular in cross section and including a self locking taper; and
  a second connector adapted to cooperate with the head component to mount the head to the intermediate connecting component, the second connector generally circular in cross section and including a self locking taper that is adapted to mount the intermediate connecting component to the head; and wherein the intermediate connecting component is adapted to rotate 360 degrees relative to each of the stem and the head;
(d) at least one set of indicia, adapted to indicate positioning of at least one component relative to at least one of the other components, in which the indicia are adapted to correspond to indicia on trial components in order to allow positioning of the prosthesis components to correspond to positioning of trial components when placed in the body; and
(e) an instrument for adjusting positioning of the components, wherein the components may be positioned without removing the components from the humerus.

87. A system according to claim 86, in which the first connector is a male component adapted to be received at least partially in a cavity in the stem.

88. A system according to claim 86 in which the second connector is a male component adapted to be received at least partially in a cavity in the head.

89. A system according to claim 86 in which the at least one set of indicia is adapted to indicate positioning of the head relative to the intermediate connecting component.

90. A system according to claim 86 in which the at least one set of indicia is adapted to indicate positioning of the intermediate connecting component relative to the stem.

91. A system according to claim 86 in which the at least one set of indicia is adapted to indicate positioning of an assembly of the head and intermediate connecting component relative to the stem.

92. A system according to claim 86 in which the at least one set of indicia is adapted to indicate positioning of an assembly of the stem and intermediate connecting component relative to the head.

93. A system according to claim 86 in which the at least one set of indicia is on a bottom face of the head.

94. A system according to claim 86 in which the at least one set of indicia is on the second connector.

95. A system according to claim 86 in which the at least one set of indicia is on the first connector.

96. A system according to the claim 86 in which the at least one set of indicia on the stem.

97. A system according to claim 86 further comprising a coupling member adapted to cooperate with the intermediate connecting component and the stem, in which the at least one set of indicia is on the coupling member.

98. A system according to claim 86 in which the indicia are calibrated laser marks.

99. A system according to claim 86 in which the intermediate connecting component and the head are coupled and removable from the stem as one component.

100. A system according to claim 99 in which the head and intermediate connecting component are coupled using a plate detent.

101. A system according to claim 99 in which the coupling prevents the head from rotating relative to the intermediate connecting component.

102. A system according to claim 86 in which the instrument comprises:
  (a) a first interface adapted to engage an intermediate connecting component; and
  (b) a second interface adapted to engage a humeral head;
  in which one of the first and second interfaces is rotatably mounted relative to the other of the first and second interfaces in order to allow at least one component to be adjusted relative to another component.

103. A system according to claim 102 in which the first interface and the second interface of the instrument rotate independently of each other and as one unit.

104. A system according to claim 102 in which the first and second interfaces are generally coaxial.

105. A system according to claim 102 in which one of the first and second interfaces translates within the other of the first and second interfaces, allowing independent engagement of one of the intermediate connecting component and head.

106. A system according to claim 102 in which one of the first and second interfaces translates within the other of the first and second interfaces, allowing engagement of both of the intermediate connecting component and head.

107. A system according to claim 102 in which the intermediate connecting component is adapted to provide rotational resistance between the intermediate connecting component and the instrument.

108. A system according to claim 102 in which the head is adapted to provide rotational resistance between the head and the instrument.

109. A system according to claim 102 in which the orientation of the head and intermediate connecting component may be adjusted in situ.

110. A system for replacement of a humeral head comprising
  (a) a modular humeral trialing system comprising:
    (1) a stem component adapted to be fitted to a resected humerus;
    (2) a trial head component not suitable for actual implantation into a patient as an orthopedic implant and adapted to approximate the size and shape of a humeral head;
    (3) an intermediate connecting component for connecting the stem to the head; and
    (4) at least one set of indicia, adapted to indicate positioning of at least one component relative to at least one of the other components, in which the indicia correspond to indicia on prosthesis components to allow positioning of the prosthesis components to correspond to positioning of trial components when placed in the body;
  (b) a modular humeral prosthesis comprising:
    (1) a stem component adapted to be fitted to a resected humerus;
    (2) a head component adapted to approximate the size and shape of a humeral head;
    (3) an intermediate connecting component for connecting the stem to the head; and
    (4) at least one set of indicia, adapted to indicate positioning of at least one component relative to at least one of the other components, in which the indicia are adapted to correspond to indicia on trial components in order to allow positioning of the prosthesis components to correspond to positioning of trial components when placed in the body; and (c) an instrument for adjusting positioning of the components.

111. A system according to claim 110 in which each of the intermediate connecting components of the system comprises:

(a) a first connector that is formed as a surface of rotation and adapted to cooperate with the stem in order to mount the intermediate connecting component to the stem; and (b) a second connector that is formed as a surface of rotation and adapted to cooperate with the head in order to mount the head to the intermediate connecting component.

112. A system according to claim 111 in which the second connector includes a self-locking tapered surface.

113. A system according to claim 111 in which the first connector is adapter to be at least partially received in a cavity of the stem and features a self-locking tapered surface.

114. A system according to claim 111 in which the first connector is a cavity formed in the second connector and adapted at least partially to receive a projection that projects the stem.

115. A system according to claim 111 in which the second connector is a cavity formed in the first connector and adapted at least partially to receive a projection that projects from the head.

116. A system according to claim 111 in which the intermediate connecting component is adapted to rotate 360 degrees relative to each of the stem and the head.

117. A system according to claim 111 in which the second connector is inclined at an angle relative to the first connector.

118. A system according to claim 111 which each of the first connector and second connector have an axis, and in which said axes are offset from each other in order to cause the first connector to be offset from the second connector.

119. A system according to claim 110 the at least one set of indicia is adapted to indicate positioning of the head relative to the intermediate connecting component.

120. A system according to claim 110 in which the at least one set of indicia adapted to indicate positioning of the intermediate connecting component relative to the stem.

121. A system according to claim 110 in which the at least one set of indicia is adapted to indicate positioning of an assembly of the head and intermediate connecting component relative to the stem.

122. A system according to claim 110 in which the at least one set of indicia is adapted to indicate positioning of an assembly of the stem and intermediate connecting component relative to the head.

123. A system according to claim 110 in which the at least one set of indicia is on a bottom face of the head.

124. A system according to claim 110 in which the at least one set of indicia is on the second connector.

125. A system according to claim 110 in which the at least one set of indicia is or the first connector.

126. A system according to claim 110 in which the at least one set of indicia is on the stem.

127. A system according to claim 110 further comprising a coupling member adapted to cooperate with the intermediate connecting component and the stem, in which the at least one set of indicia is on the coupling member.

128. A system according to claim 110, in which the indicia are calibrated laser marks.

129. A system according to claim 110 in which the intermediate connecting component and the head are coupled and movable from the stem as one component.

130. A system according to claim 129 in which the head and intermediate connecting components are coupled using a plate detent.

131. A system according to claim 129 in which the coupling prevents the head from relative to the intermediate connecting component.

132. A system according to claim 129 wherein the instrument comprises a first interface and a second interface, in which the head and intermediate connecting component are adapted to receive the instrument.

133. A system according to claim 132 in which the intermediate connecting component engages the first interface of instrument and the head engages the second interface of the instrument.

134. A system according to claim 132 in which the first interface and the second interface of the instrument rotate independently and as one unit.

135. A system according to claim 132 in which the first and second interfaces are generally coaxial.

136. A system according to claim 132 in which one of the first and second interfaces translates within the other of the first and second interfaces, allowing independent engagement of one of the intermediate connecting component and head.

137. A system according to claim 132 in which one of the first and second interfaces translates within the other of the first and second interfaces, allowing engagement of both of the intermediate connecting component and head.

138. A system according to claim 132 in which the intermediate connecting component is adapted to provide rotational resistance between the intermediate connecting component and the instrument.

139. A system according to claim 132 in which the head is adapted to provide rotational resistance between the head and the instrument.

140. A system according to claim 132 in which the orientation of the head and intermediate connecting component may be adjusted in situ.

141. A system for replacement of a humeral head comprising (a) a modular humeral trialing system comprising:

(1) a stem component adapted to be fitted to a resected humerus;

(2) a trial head component not suitable for actual implantation into a patient as an orthopedic implant and adapted to approximate the size and shape of a humeral head, the head featuring a bottom face;

(3) an intermediate connecting component for connecting the stem to the head, the intermediate connecting component including:

a first connector adapted to cooperate with the stem component to mount the stem to the intermediate connecting component, the first connector generally circular in cross section and including a self locking taper; and a second connector adapted to cooperate with the head component to mount the head to the intermediate connecting component, the second connector generally circular in cross section and including a self locking taper that is adapted to mount the intermediate connecting component to the head;

(4) at least one set of indicia, adapted to indicate positioning of at least one component relative to at least one of the other components, in which the indicia correspond to indicia on prosthesis components to allow positioning of the prosthesis components to correspond to positioning of trial components when placed in the body;

(b) a modular humeral prosthesis for use in replacement of the humeral head of a humerus, comprising:
(1) a stem component adapted to be fitted to a resected humerus;
(2) a head component adapted to approximate the size and shape of a humeral head, the head featuring a bottom face;
(3) an intermediate connecting component for connecting the stem to the head, the intermediate connecting component including:
a first connector adapted to cooperate with the stem component to mount the stem to the intermediate connecting component, the first connector generally circular in cross section and including a self locking taper; and
a second connector adapted to cooperate with the head component to mount the head to the intermediate connecting component, the second connector generally circular in cross section and including a self locking taper that is adapted to mount the intermediate connecting component to the head;
(4) at least one set of indicia, adapted to indicate positioning of at least one component relative to at least one of the other components, in which the indicia are adapted to correspond to indicia on trial components in order to allow positioning of the prosthesis components to correspond to positioning of trial components when placed in the body; and (c) an instrument for adjusting positioning of the components.

142. A system according to claim 141 in which each of the at least one sets of indicia is adapted to indicate positioning of the head relative to the intermediate connecting component.

143. A system according to claim 141 in which each of the at least one sets of indicia is adapted to indicate positioning often intermediate connecting component relative to the stem.

144. A system according to claim 141 each of the at least one sets of indicia is adapted to indicate positioning of an assembly of the head and intermediate connecting component relative to the stem.

145. A system according to claim 141 each of the at least one sets of indicia is adapted to indicate positioning of an assembly of the stem and intermediate connecting component relative to the head.

146. A system according to claim 141 in which each of the at least one sets of indicia is on a bottom face of the head.

147. A system according to claim 141 in which each of the at least one sets of indicia is on the second connector.

148. A system according to claim 141 in which each of the at least one sets of indicia is on the first connector.

149. A system according to claim 141 in which each of the at least one sets of indicia is on the stem.

150. A system according to claim 141 in which the indicia are calibrated laser marks.

151. A system according to claim 141 in which the instrument comprises:
(a) first interface adapted to engage an intermediate connecting component; and
(b) a second interface adapted to engage a head component;
in which one of the first and second interfaces is rotatably mounted relative to the other of the first and second interfaces in order to allow at least one component to be adjusted relative to another component.

152. A system according to claim 151 in which the first interface and the second interface of the instrument rotate independently of each other and as one unit.

153. A system according to claim 151 in which the first and second interfaces are generally coaxial.

154. A system for replacement of a humeral head comprising:
(a) a modular humeral prosthesis; and
(b) an instrument for adjusting positioning of components of the prosthesis, comprising
(i) a first interface adapted to engage an intermediate connecting component; and
(ii) a second interface adapted to engage a humeral head;
in which one of the first and second interfaces is rotatably mounted relative to the other of the first and second interfaces in order to allow at least one component to be adjusted relative to another component.

155. A system according to claim 154 in which the mounting of the first and second interfaces allows at least one of the intermediate connecting component or the head to be adjusted relative to the other.

156. A system according to claim 154 in which the first and second interfaces of the instrument rotate independently and as one unit.

157. A system according to claim 154 in which the first and second interfaces of the instrument are generally coaxial.

158. A system according to claim 154 in which the first and second interfaces of the instrument are secured together to prevent separation.

159. A system according to claim 154 in which one of the first and second interfaces of the instrument translates within the other of the first and second interfaces, allowing independent engagement of one of the intermediate connecting component and head.

160. A system according to claim 154 in which one of the first and second interfaces of the instrument translates within the other of the first and second interfaces, allowing engagement of both of the intermediate connecting component and head.

161. A system according to claim 154 further comprising indicia for mapping positioning of at least one of the components relative to at least one other component.

162. A system according to claim 161 in which the indicia are on the instrument.

163. A system for replacement of a humeral head comprising:
(a) a modular humeral prosthesis; and
(b) an instrument for adjusting positioning of components of the prosthesis, comprising:
(i) a first interface adapted to engage an intermediate connecting component;
(ii) a second interface adapted to engage a humeral head; and
(iii) at least one set of indicia on at least one of the instrument, the intermediate connecting component, and the head, for mapping positioning of at least one of the components relative to at least one other component; in which one of the first and second interfaces is rotatably mounted relative to the other of the first and second interfaces in order to allow at least one component to be adjusted relative to another component, in which the first and second interfaces rotate independently and as one unit.

164. A modular trialing system and humeral prosthesis kit for replacement of the humeral head of a humerus, comprising:
(a) a stem to be fitted to a resected humerus;
(b) a plurality of trial heads, each trial head not suitable for actual implantation into a patient as an orthopedic implant and wherein each trial head is sized and configured to approximate the humeral head;
(c) a plurality of prosthetic heads sized and configured to approximate the humeral head;
(d) a plurality of intermediate connecting components of which one may be selected to connect the stem to a trial head, comprising trial intermediate connecting components and prosthesis intermediate connecting components;
(e) at least one set of indicia on at least one of the trial components, in which the indicia correspond to indicia on prosthesis components to allow positioning of the prosthesis components to correspond to positioning of trial components when placed in the body;
(f) at least one set of indicia on at least one of the prosthesis components, in which the indicia are adapted to correspond to indicia on trial components in order to allow positioning of the prosthesis components to correspond to positioning of trial components when placed in the body; and
(g) an instrument for adjusting positioning of at least one of the components relative to another component.

165. A system and kit according to claim 164 in which each intermediate connecting member comprises:
(a) a first connector that is formed as a surface of rotation and adapted to cooperate with the stem in order to mount the intermediate connecting component to the stem; and
(b) a second connector that is formed as a surface of rotation and adapted to cooperate with the head in order to mount the head to the intermediate connecting component.

166. A system and kit according to claim 165 in which the intermediate connecting components of the kit further comprise:
at least one intermediate connecting component in which the surfaces of rotation of each of the first and second connectors share the same axis of rotation;
at least one intermediate connecting component in which the surfaces of rotation of each of the first and second connectors are generally parallel to each other but offset; and
at least one intermediate connecting component in which the surfaces of rotation of each of the first and second connectors are inclined at an angle relative to each other, causing the first and second connectors to be inclined at an angle relative to each other.

167. A system and kit according to claim 165 in which the second connector includes a self-locking tapered surface.

168. A system and kit according to claim 165 in which the first connector is adapted to be at least partially received in a cavity of the stem and features a self-locking tapered surface.

169. A system and kit according to claim 165 in which the first connector is a cavity formed in the second connector and adapted at least partially to receive a projection that projects from the stem.

170. A system and kit according to claim 165 in which the second connector is a cavity formed in the first connector and adapted at least partially to receive a projection that projects from the head.

171. A system and kit according to claim 165 in which the intermediate connecting component is adapted to rotate 360 degrees relative to stem head.

172. A system and kit according to claim 165 in which the second connector is inclined at an angle relative to the first connector.

173. A system and kit according to claim 165 in which each of the first connector and second connector have an axis, and in which said axes are offset from each other in order to cause the first connector to be offset from the second connector.

174. A system and kit according to claim 164 in which each of the at least one set of indicia is adapted to indicate positioning of the head relative to the intermediate connecting component.

175. A system and kit according to claim 164 in which each of the at least one set of indicia is adapted to indicate positioning of the intermediate connecting component relative to the stem.

176. A system and kit according to claim 164 in which each of the at least one set of indicia is adapted to indicate positioning of an assembly of the head and intermediate connecting component relative to the stem.

177. A system and kit according to claim 164 in which each of the at least one set of indicia is adapted to indicate positioning of an assembly of the stem and intermediate connecting component relative to the head.

178. A system and kit according to claim 164 in which each of the at least one set of indicia is on a bottom face of the head.

179. A system and kit according to claim 164 in which each of the at least one set of indicia is on the second connector.

180. A system and kit according to claim 164 in which each of the at least one set of indicia is on the first conductor.

181. A system according to claim 164 in which each of the at least one set of indicia is on the stem.

182. A system and kit according to claim 164 further comprising a coupling member adapted to cooperate with the trial intermediate connecting component and stem, in which the at least one set of indicia is on the coupling member.

183. A system and kit according to claim 164 further comprising a coupling member adapted to cooperate with the prosthesis intermediate connecting component and stem, in which the at least one set of indicia is on the coupling member.

184. A system and kit according to claim 164 in which the indicia are calibrated laser marks.

185. A system and kit according to claim 164 in which the instrument comprises:
(a) a first interface adapted to engage an intermediate connecting component; and
(b) a second interface adapted to engage a humeral head;
in which one of the first and second interfaces is rotatably mounted relative to the other of the first and second interfaces in order to allow at least one component to be adjusted relative to another component.

186. A system and kit according to clam 185 in which the first interface and the second interface of the instrument rotate independently of each other and as one unit.

187. A system and kit according to claim 185 in which the first and second interfaces are generally coaxial.

188. A method of replacing a humeral head in a patient, comprising:
  (a) resecting the proximal end of the humerus to remove the head and expose the medullary canal of the humerus;
  (b) inserting a stem of a prosthesis into the medullary canal of the resected humerus, the prosthesis comprising:
    (i) the stem;
    (ii) a head adapted to approximate the size and shape of a humeral head;
    (iii) one of a plurality of intermediate connecting components for connecting the stem to the head, each intermediate connecting component including:
      a first connector formed as a surface of rotation and adapted to cooperate with the stem in order to mount the intermediate connecting component to the stem; and
      a second connector formed as a surface of rotation and adapted to cooperate with the head in order to mount the head to the intermediate connecting component;
    the plurality of intermediate connecting components including at least some members having different angles of inclination between their first and second connectors; and
    (iv) at least one set of indicia adapted to indicate positioning of at least one component relative to at least one of the other components;
  (c) selecting a trial prosthesis that provides a desired angle of inclination of the head relative to the humerus; the trial comprising:
    (i) a trial head not suitable for actual implantation into a patient as an orthopedic implant and adapted to approximate the size and shape of a humeral head;
    (ii) one of a plurality of intermediate connecting components for connecting the stem to the head; and
    (iii) at least one set of indicia adapted to indicate positioning of at least one component relative to at least one of the other components;
  (d) adjusting the version and inclination of the trial intermediate connecting component using an instrument;
  (e) mounting the trial intermediate connecting component to the stem;
  (f) mounting the trial head to the intermediate connecting component;
  (g) adjusting trial head center positioning using an instrument;
  (h) adjusting inclination, version and eccentricity as required;
  (i) noting the sizes and relative positions of at least two of the of the trial intermediate connecting component, trial head, and stem;
  (j) matching geometry and positioning of trial intermediate connecting component, trial head and stem to prosthesis intermediate connecting component, head and stem: and
  (k) installing the prosthesis in the body.

189. A method according to claim 188 in which each of the trial and prosthesis intermediate connecting components comprises:
  (a) a first connector that is formed as a surface of rotation and adapted to cooperate with the stem in order to mount the intermediate connecting component to the stem; and
  (b) a second connector that is formed as a surface of rotation and adapted to cooperate with the head in order to mount the head to the intermediate connecting component.

190. A method according to claim 189 in which the second connector includes a self-locking tapered surface.

191. A method according to claim 189 in which the first connector is adapted to be at least partially received in a cavity of the stem and features a self-locking tapered surface.

192. A method according to claim 189 in which the first connector is a cavity formed in the second connector and adapted at east partially to receive a projection that projects from the stem.

193. A method according to claim 189 the second connector is a cavity formed in the first connector and adapted at least partially to receive a projection that projects from the head.

194. A method according to claim 189 in which the intermediate connecting component is adapted to rotate 360 degrees relative to each of the stem and the head.

195. A method according to claim 189 in which the second connector is inclined at an angle relative to the first connector.

196. A method according to claim 189 in which each of the first connector and second connector have an axis, and in which said axes are offset from each other in order to cause the first connector to be offset from the second connector.

197. A method according to claim 189 in winch each of the at least one set of indicia is adapted to indicate positioning of the head relative to the intermediate connecting component.

198. A method according to claim 188 in which each of the at least one set of indicia is adapted to indicate positioning of the intermediate connecting component relative to the stem.

199. A method according to claim 188 in which each of the at least one set of indicia is adapted to indicate positioning of an assembly of the head and intermediate connecting component relative to the stem.

200. A method according to claim 188 in which each of the at least one set of indicia is adapted to indicate positioning of an the stem and intermediate connecting component relative to the head.

201. A method according to claims 188 in which each of the at least one set of indicia is on a bottom face of each of the trial head and prosthesis head.

202. A method according to claim 188 each of the at least one set of indicia is on each of the trial second connector and prosthesis second connector.

203. A method according to claim 188 in which each of the at least one set of indicia is on each of the trial first connector and prosthesis first connector.

204. A method according to claim 188 in which each of the at least one set of indicia is on the stem.

205. A method according to claim 188 further comprising a coupling member adapted to cooperate with the trial intermediate connecting component and the stem, in which the at east one set of indicia is on the coupling member.

206. A method according to claim 188 further comprising a prosthesis coupling member adapted to cooperate with the prosthesis intermediate connecting component and the stem, in which the at least one set of indica is on the coupling member.

207. A method according to claim 188 in which the indicia are calibrated laser marks.

208. A method according to claim 188 in which the adjusting is accomplished using an instrument comprising a first interface and a second interface, in which each of the trial head and trial intermediate connecting component and prosthesis head and prosthesis intermediate connecting component are adapted to receive the instrument.

209. A method according to claim 208 in which the first interface and the second interface of the instrument rotate independently of each other and as one unit.

210. A method according to claim 208 in which the first and second interfaces are generally coaxial.

211. A method according to claim 208 in which one of the first and second interfaces translates within the other of the first and second interfaces, allowing independent engagement of one of the trial intermediate connecting component, trial head, prosthesis intermediate connecting component and prosthesis head.

212. A method according to claim 208 in which one of the first and second interfaces translates within the other of the first and second interfaces, allowing engagement of both of the intermediate connecting component and head.

213. A method according to claim 208 in which each of the intermediate connecting components is adapted to provide rotational resistance between the intermediate connecting component and the instrument.

214. A method according to claim 208 in which each of the heads is adapted to provide rotational resistance between the head and the instrument.

215. A method according to claim 208 in which the orientation of each of the head and intermediate connecting components may be adjusted in situ.

* * * * *